United States Patent [19]

Greenspan

[11] Patent Number: 4,551,429

[45] Date of Patent: Nov. 5, 1985

[54] **STIMULATION OF ANTIGEN PRODUCTION BY *BORDETELLA PERTUSSIS***

[75] Inventor: George Greenspan, Narberth, Pa.

[73] Assignee: American Home Products Corporation, New York, N.Y.

[21] Appl. No.: 532,642

[22] Filed: Sep. 15, 1983

[51] Int. Cl.$^4$ .................. C12N 1/38; C12N 1/10; C12N 1/00; A61K 39/02; A61K 39/10; C12P 21/00; C12P 21/02

[52] U.S. Cl. .................................. 435/68; 435/70; 435/243; 435/244; 435/255; 424/88; 424/92; 260/112 R

[58] Field of Search ............... 435/68, 70, 240, 253, 435/244, 813, 243; 424/88, 92, 85; 260/112 R

[56] References Cited

U.S. PATENT DOCUMENTS

| | | | |
|---|---|---|---|
| 2,240,969 | 5/1941 | Voigt et al. | 167/68 |
| 4,455,297 | 6/1984 | Syukuda et al. | 424/92 |

FOREIGN PATENT DOCUMENTS

| | | | |
|---|---|---|---|
| 0089245 | 9/1983 | European Pat. Off. | 424/85 |
| 3319714 | 12/1983 | Fed. Rep. of Germany | 435/68 |

OTHER PUBLICATIONS

Imaizumi et al., Abstracts of the 1982 ICAAC, p. 109, Abstract 251, "A New Shaking Culture Method for the Production of Pertussis Component Vaccine . . . ".

Arai et al., Biochimica et Biophysica Acta, Vo. 444, (1976), pp. 765–782, "Separation and Characterization of Two Distinct Hemagglutinins Contained in Purified Leukocytosis-Promoting Factor from JJ *Bordetella pertussis*.

Botre et al., *Chem. Abst.*, vol. 62, 1965, p. 966, "Influence of Polymers on *Penicillium chrysogenum* Fermentation".

Hewlett et al., J. of Bact., vol. 127(2), Aug. 1976, pp. 890–898, "Soluble Adenylate Cyclase from the Culture Medium of *Bordetella pertussis*: Purification and Characterization".

Cohen et al., *Amer. J. Public Health*, Apr. 1946, pp. 371–376, vol. 36, "Pertussis Vaccine Prepared with Phase-I Cultures Grown in Fluid Medium".

Botre et al., "Influenza di Alcuni Polimeri Nella Fermentazione del 'Penicillium Chrysogenum', *Farmaco. Ed. Pract.* 19, 507ff, (1964), (translated portions only).

*Primary Examiner*—Thomas G. Wiseman
*Assistant Examiner*—Robin Lyn Teskin
*Attorney, Agent, or Firm*—George Tarnowski

[57] ABSTRACT

A method for the elaboration of large quantities of *Bordetella pertussis* protective antigens useful in the production of acellular vaccines for prevention of whooping cough.

2 Claims, No Drawings

STIMULATION OF ANTIGEN PRODUCTION BY BORDETELLA PERTUSSIS

The present invention provides a method for the elaboration of large quantities of *Bordetella pertussis* protective antigens useful in the production of acellular vaccines protective against whooping cough.

Most conventionally prepared pertussis vaccines employ statically grown inactivated whole pathogens, i.e., whole inactivated cells of *Bordetella pertussis*. However, these pathogens often cause a number of side effects, e.g., local pain and inflammation at the site of vaccine administration, fever caused by the pathogens' endotoxin and in certain cases even serious neurological complications such as encephalitis.

Accordingly, efforts have been made to prepare less reactogenic pertussis vaccines, especially acellular pertussis vaccines containing the antigenic component responsible for eliciting the desired immune response in the host. The basic process for obtaining such a component requires a shaken culture, whereby the antigenic material is secreted into the surrounding medium, facilitating isolation of the purified component. However, the amount of product found in the cell-free broth is normally relatively small, even when the *B. pertussis* cells are grown in a shaken culture.

*Bordetella pertussis* elaborates a hemagglutinin which is composed of the protective antigens fimbrial hemagglutinin (FHA) and leucocytosis promoting factor hemagglutinin (LPFHA). It is the production of the two antigenic proteins that is desired. According to a recent report, researchers were able to effectuate a significant increase in the production of pertussis LPFHA from a shaken culture by the addition of 2,6-di-O-methylated $\beta$-cyclodextrin to the shaken culture medium (see Imaizumi, A., et al., "A New Shaking Culture Method for the Production of Pertussis Component Vaccine Using 2,6-di-O-methylated $\beta$-cyclodextrin." Abstract, *22nd Interscience Conference on Antimicrobial Agents and Chemotherapy*, p. 109, Oct. 4-6, 1982, Miami Beach, Fla.).

There has now been found a method for greatly enhancing the production of both fimbrial hemagglutinin and leucocytosis promoting factor hemagglutinin by use of a shaken *B. pertussis* culture to which is added the water soluble polymer, polyvinyl alcohol.

The method for preparing the protective antigenic hemagglutinin of *B. pertussis* consisting of fimbrial hemagglutinin and leucocytosis promoting factor hemagglutinin comprises propagating a *Bordetella pertussis* culture in an aqueous nutrient medium containing a source of carbohydrate, a source of organic nitrogen and inorganic salts under submerged aerobic conditions with shaking of the culture medium, transferring an inoculum of the first stage growth of *Bordetella pertussis* into an aqueous nutrient medium containing sources of organic nitrogen, vitamins and inorganic salts and with the addition thereto of polyvinyl alcohol of molecular weight of about 1500 to about 16,000, growing said inoculum in said nutrient medium under submerged aerobic conditions, with shaking, until substantial hemagglutinating activity is imparted thereto, separating the *B. pertussis* cells from the medium and recovering the protective antigenic hemagglutinin-containing supernatant.

The method of the invention is essentially a two-step fermentation. In the first step, a culture of *Bordetella pertussis*, preferably the Tohama Phase I strain, is propagated in an aqueous medium containing a source of carbohydrate, a source of organic nitrogen and inorganic salts, under submerged aerobic conditions with shaking. The preferred culture medium is modified Cohen-Wheeler medium [see Cohen and Wheeler, "Pertussis Vaccine Prepared With Phase-I Cultures Grown in Fluid Medium," *Am. J. Public Health* 36: 371-76 (1946)]. The first stage propagation is carried out for a period of 18-24 hours at a temperature of 35°-37° C. with shaking at 140 RPM. The optical density (O.D.) reading for growth at 650 nm in a spectrophotometer ranges from 1.0 to 1.6.

In the second stage, inoculum from the first stage is transferred to another aqueous nutrient medium containing sources of organic nitrogen, vitamins and inorganic salts and further growth is continued under submerged aerobic conditions with shaking of the culture. In this instance, however, the culture medium is supplemented by the addition of polyvinyl alcohol of molecular weight of about 1500 to about 16,000. The preferred second stage medium is modified Stainer-Scholte medium [see Hewlett and Wolff, "Soluble Adenylate Cyclase from the Culture Medium of *Bordetella pertussis*," *J. Bacteriol* 127: 890-98 (1976)]. The culture medium is supplemented at the rate of about 0.5-2.0 g/L with polyvinyl alcohol preferably having a molecular weight of about 10,000. The medium with the polyvinyl alcohol is inoculated to give an optical density reading of 0.09-0.12 at 650 nm. The cultures are incubated at 35°-37° C. with shaking at 140-150 RPM for a period of 3-6 days.

At the end of the specified period, the whole *B. pertussis* cells are separated from the culture medium by centrifugation and the resulting supernatant is processed by conventional means to separate the protective hemagglutinins. For example, after adjustment of the pH, the supernatant can be subjected to filtration chromatography to purify the recovered hemagglutinins.

The activity of the hemagglutinins recovered in the supernatant and the extent of production of the hemagglutinins via the two step, polyvinyl alcohol supplemented shaken culture method of the invention is measured in a standard hemagglutination microtiter assay using goose and chick erythrocytes. The assay and the results obtained therefrom are given in the Examples.

The process of the present invention provides a product containing the protective antigens of *B. pertussis*, which product can be used in the preparation of pertussis vaccines for the prophylaxis of whooping cough, or for the manufacture of pertussis antisera to be used for therapeutic or diagnostic purposes. The pertussis vaccines prepared from the product obtained from the method of the invention can be administered orally or parenterally.

The protective antigenic hemagglutinin-containing component obtained by the method of the invention may be protected by adding antimicrobial preservation agents thereto. In order to prepare polyvalent vaccines, the purified protective component may be mixed in the usual manner with other antigens and/or toxoids.

The following Examples illustrate the invention.

EXAMPLE 1

Three slants of Bordet-Gengou blood agar with three day growth of *Bordetella pertussis*, Tohama Phase I strain, are each washed with 10 ml of modified Cohen-Wheeler medium of the following composition:

|  | g/l |
| --- | --- |
| Casamino Acids (Difco) | 10.0 |
| NaCl | 2.5 |
| KH$_2$PO$_4$ | 0.5 |
| MgCl$_2$.6H$_2$O | 0.4 |
| Soluble Starch | 1.5 |
| CaCl$_2$ | 0.01 |
| FeSO$_4$.7H$_2$O | 0.01 |
| CuSO$_4$.5H$_2$O | 0.00075 |
| Cysteine.HCl.H$_2$O | 0.03342 |
| Tris (hydroxymethyl) aminomethane | 6.07 |
| DL-Glutamic Acid.H$_2$O | 0.23 |
| Nicotinamide | 0.03 |
| Reduced Glutathione | 0.01 |
| Deionized, distilled H$_2$O | q.s. to 1 l. |

All ingredients except FeSO$_4$.7H$_2$O and reduced glutathione are dissolved in water, the pH adjusted to 7.2 with 6N HCl and the medium autoclaved at 121° C. for 20 minutes. After cooling, solutions of FeSO$_4$.7H$_2$O and reduced glutathione sterilized by membrane filtration are added aseptically to the medium.

The suspensions are transferred to three 500 ml. Erlenmeyer flasks each containing 190 ml of modified Cohen-Wheeler medium. The flasks are placed on a rotary shaker with a 2 in. circular orbit and agitated at 140 RPM, 35° C. After 21 hours of incubation, Gram stains are made of the contents of each flask, and the slides are examined microscopically for purity. The cell suspensions are pooled, and an O.D. reading is taken at 650 nm on a Bausch & Lomb Spectrophotometer, Model Spectronic 20; a value of 1.35 is obtained. The transfer of 11.5 ml of the Cohen-Wheeler inoculum to a 500 ml flask with 150 ml of modified Stainer-Scholte medium gives a suspension with the desired O.D. reading of 0.11.

The Stainer-Scholte (modified) medium is prepared in two sections:

| 1. Basal Medium | g/l |
| --- | --- |
| Sodium glutamate | 10.72 |
| l-proline | 0.24 |
| NaCl | 2.5 |
| KH$_2$PO$_4$ | 0.5 |
| KCl | 0.2 |
| MgCl$_2$.6H$_2$O | 0.1 |
| CaCl$_2$ | 0.02 |
| Tris (hydroxymethyl) aminomethane | 1.525 |
| Deionized, distilled H$_2$O | q.s. to 1 l. |

The pH is adjusted to 7.6 with concentrated HCl, and the flasks are autoclaved at 121° C. for 15 minutes.

| 2. Supplement | |
| --- | --- |
| l-cysteine | 0.4 g. |

Added to 10 ml concentrated HCl and q.s. with deionized, distilled water to 100 ml.

| FeSO$_4$.7H$_2$O | 0.1 g. |
| --- | --- |
| Ascorbic Acid | 0.2 g. |
| Niacin | 0.04 g. |
| Glutathione, reduced | 1.0 g. |

The ingredients are dissolved without heating, and the solution is sterilized by membrane filtration. Ten ml of the supplemental solution is added per liter of basal medium immediately prior to use. The pH of the medium is again adjusted to 7.6, aseptically.

The second stage of the fermentation is carried out in 500 ml flasks with 150 ml of complete Stainer-Scholte (modified) medium. These flasks, which have been supplemented in duplicate with various levels of polyvinyl alcohol (PVA), M.W. ca. 10,000, are each inoculated with 11.5 ml of first stage growth of *B. pertussis* grown in modified Cohen-Wheeler medium for 21 hours. Polyvinyl alcohol (PVA), M TABLE 1-continued

| | | End Point Readings Obtained In Microtiter Assay For Hemagglutination | | | | | | | |
|---|---|---|---|---|---|---|---|---|---|
| | | 1 Day | | 2 Day | | 3 Day | | 6 Day | |
| | PVA g/l | Chick Blood | Goose Blood | Chick Blood | Goose Blood | Chick Blood | Goose Blood | Chick Blood | Goose Blood |
| 2. | — | <2 | 4, ±8 | <2 | 2, ±4 | <2 | <2 | — | — |
| B1. | 0.5 | 64 | 512 | 128 | 2048 | 64, ±128 | 1024 | — | — |
| 2. | 0.5 | 64 | 512 | 128 | 2048 | 64, ±128 | 1024 | — | — |
| C1. | 1.0 | 128 | 512 | 1024 | 4096 | 512 | 4096, ±8192 | 64, ±128 | 1024 |
| 2. | 1.0 | 64, ±128 | 512 | 256 | 4096 | 256, ±512 | 4096, ±8192 | 128 | — |
| C3. | 1.0 | 64 | 512 | 512 | 4096 | 512 | 4096, ±8192 | 512, ±1024 | 4096 |
| 4. | 1.0 | 128 | 2048 | 256, ±512 | 4096 | 256, ±512 | 4096, ±8192 | 1024 | 2048 |
| D1. | 1.5 | 128 | 512 | 512, ±1024 | 4096 | 512 | 4096, ±8192 | 1024, ±2048 | 4096 |
| 2. | 1.5 | 128 | 1024 | 256, ±512 | 4096 | 512 | 4096 | 512 | 1024 |
| E1. | 2.0 | 256 | 512, ±1024 | 512 | 4096 | 512 | 4096 | 128, ±256 | 4096 |
| 2. | 2.0 | 128, ±256 | 512, ±1024 | 512 | 4096 | 1024 | 4096 | 512, ±1024 | 4096 |
| F1. | 1.5 | 128. ±256 | 1024 | 512 | 4096 | 512, ±1024 | 8192 | 8 | 64 |
| 2. | 1.5 | 128, ±256 | 2048 | 256, ±512 | 4096 | 256, ±512 | 4096, ±8192 | <2 | 8 |
| G1. | — | <2 | 2 | <2 | ±2 | <2 | <2 | — | — |
| 2. | — | <2 | 2 | <2 | <2 | <2 | <2 | — | — |
| H1. | 1.5 | 128, ±256 | 1024 | 2048 | 4096 | 512, ±1024 | 4096 | <2 | 8 |
| 2. | 1.5 | 128 | 1024 | 512 | 4096 | 512, ±1024 | 4096, ±8192 | <2 | 32 |
| I1. | — | <2 | 2 | <2 | <2 | <2 | <2 | — | — |
| 2. | — | <2 | 2 | <2 | <2 | <2 | <2 | — | — |

The titer assay results show that shaken cultures containing from 0.5 to 2.0 g/l of polyvinyl alcohol produce a very greatly enhanced quantity of protective pertussis hemagglutinins. This method makes possible the preparation of acellular pertussis vaccines which are prophylactic for whooping cough and which have minimal side effects.

What is claimed is:

1. In a method for preparing the protective antigenic hemagglutinin of *Bordetella pertussis*, consisting of fimbrial hemagglutinin and leucocytosis promoting factor hemagglutinin, which comprises propagating a *Bordetella pertussis* culture in an aqueous nutrient medium containing a source of carbohydrate, a source of organic nitrogen and inorganic salts, under submerged aerobic conditions with shaking of the culture medium, transferring an inoculum of the first stage growth of *Bordetella pertussis* into an aqueous nutrient medium containing sources of organic nitrogen, vitamins and inorganic salts, growing said inoculum in said medium under submerged aerobic conditions, with shaking, separating the *Bordetella pertussis* cells from the medium and recovering the protective antigenic hemagglutinin-containing supernatant, the improvement which comprises adding to the non-carbohydrate containing aqueous nutrient medium polyvinyl alcohol having a molecular weight ranging from about 1,500 to about 16,000 at the level of 0.5 to 2.0 g/l of medium, whereby substantially enhanced hemagglutinating activity is imparted thereto.

2. The method of claim 1, wherein the polyvinyl alcohol has a molecular weight of 10,000.

* * * * *